United States Patent [19]
Zaharkin et al.

[11] Patent Number: 5,474,088
[45] Date of Patent: Dec. 12, 1995

[54] DEVICE FOR MEASURING MOTION CHARACTERISTICS OF A HUMAN JOINT

[75] Inventors: John M. Zaharkin, N. Tonowanda; Michael S. Zaharkin, Rochester, both of N.Y.

[73] Assignee: The Research Foundation of State University of New York, Albany, N.Y.

[21] Appl. No.: 163,640

[22] Filed: Dec. 9, 1993

[51] Int. Cl.⁶ .................................................. A61B 5/103
[52] U.S. Cl. ............................................ 128/782; 128/897
[58] Field of Search ............................... 128/774, 781, 128/782, 897, 898; 482/8, 900, 901

[56] References Cited

U.S. PATENT DOCUMENTS

| | | | |
|---|---|---|---|
| 3,020,639 | 2/1962 | Karpovich et al. | 128/782 |
| 3,929,335 | 12/1975 | Malick | 482/8 |
| 4,436,099 | 3/1984 | Raftopoulos | 128/782 |
| 4,442,606 | 4/1984 | Graham et al. | |
| 4,571,834 | 2/1986 | Fraser et al. | |
| 4,667,685 | 5/1987 | Fine | 128/782 |
| 4,804,001 | 2/1989 | McLeod, Jr. | 128/782 |
| 5,012,819 | 5/1991 | Marras et al. | 128/781 |
| 5,027,688 | 7/1991 | Suzuki et al. | 128/782 X |
| 5,052,379 | 10/1991 | Airy et al. | 482/8 X |
| 5,220,308 | 6/1993 | Batzdorff et al. | 128/782 X |
| 5,263,492 | 11/1993 | Voyce | 128/782 |

FOREIGN PATENT DOCUMENTS 9302621  2/1993  WIPO ................................... 128/774

*Primary Examiner*—Angela D. Sykes
*Assistant Examiner*—Samuel Gilbert

[57] ABSTRACT

A device is disclosed which measures motion characteristics of a human joint. The device includes a patient-worn brace mechanism having two pivotally-connected arms, the pivot point being provided by a rotary-controlled angle detector. Signals from the angle detector are received in a modular housing which houses elements a microprocessor system. The device includes a computer program enabling the microprocessor system to process the signals and to measure a human joint's average angular velocity.

15 Claims, 3 Drawing Sheets

DEVICE FOR MEASURING MOTION CHARACTERISTICS OF A HUMAN JOINT

BACKGROUND OF THE INVENTION

In diagnosing a patient suffering from an injury or a condition generally affecting a major limb, doctors, physical therapists, and other health care workers find it useful to analyze data related to motion characteristics of the affected limb's joint.

Devices have long been available which aid in the measurement of relative angular position or angular displacement of a patient's joint. The first of these devices were simple in structure comprising essentially two arms pivotally connected at a hinge with one of said arms having a gage extending therefrom and intersecting the other arm to provide a mechanical readout of angular position similar to that provided by a protractor. The early devices were simply applied across a fully contracted, then a fully extended pair of body part members. By noting the difference between the contracted-position and extended-position measurements users of such devices were able to roughly estimate angular displacement. The first patient-worn angular displacement measuring devices were rather crudely attached to subject body part members and measured angular position by the same mechanical, protractor-like means.

The past two decades have seen considerable activity in the improvement of devices capable of measuring the angular displacement between two body part members connected at a common joint. U.S. Pat. No. 4,436,099, Raftopoulus, describes an improved support means for patient-worn angular displacement measuring devices. The improved device overcomes deficiencies of prior devices whose support means, it is said, encumbered natural body part movement and therefore gave rise to distorted measurements of angular displacement. The Raftopoulus patent also describes means for digitally displaying angular position and displacement comprising an encoder in combination with a counter circuit and a display unit.

U.S. Pat. No. 4,442,606, Graham et al., describes a device for measuring the angle made by two bones connected at a common joint comprising two arms connected by a rotary potentiometer. The potentiometer output is fed through a decoding device and then to a digital readout device. Preferably, the potentiometer output is simply inputted into a digital voltmeter whose gain is adjusted such that its display indicates relative angular position, either in degrees or radians.

U.S. Pat. No. 4,667,685, Fine, describes a therapeutic device providing visual feedback to a patient exercising an injured joint. An analog signal generated by a transducer mounted to a brace mechanism activates a series of light-emitting diodes in succession as a patient moves his or her joint to increase the transducer's output voltage. By observing the LED array, a patient is provided a graphical representation of angular displacement, and an indication of the distance needed to be moved to reach a preset target displacement angle.

The usefulness of data respecting the range of motion of a patient's injured joint has long been recognized. Fortunately, as the cited prior art illustrates, devices are now available which greatly improve the ease and the accuracy with which joint position and displacement information is obtained and displayed. But while devices currently available reliably measure and display data pertaining to the range of motion of a patient's joint, none of the devices described in the cited prior art can measure and display data pertaining to the speed with which a patient's joint is moved.

Obtaining a measurement for angular velocity of joint-connected body part members with currently available devices requires complex data manipulation. One publication that recognizes the usefulness of data respecting angular velocity of a moving joint, U.S. Pat. No. 5,012,819, Marras et al., describes a device which can record the angular position versus time, relative to a predetermined start position for each of any three planes of motion of a human spine. Failing to teach a means for electronic measurement and display, the Marras patent discloses that the rate of angle change of any of the three planes of spine movement can be calculated by analyzing the data pertaining to position versus time for the subject plane, then differentiating said data to obtain a value for instantaneous angular velocity at any point in time.

In view of the fact that important diagnostic information can be gained by observing data pertaining to the speed with which a joint is moved which cannot otherwise be gained by merely observing the range of motion of body part members connected at said joint, it is a principal object of the present invention to provide, without complex data manipulation, a device which electronically measures and displays the average angular velocity of a moving joint.

SUMMARY OF THE INVENTION

In designing the disclosed device the inventors observed that angular velocity of a limb about a joint can be divided into three phases: a startup phase, a middle phase, and a slowdown phase. During both the startup phase, where angular momentum is accumulated and the slowdown phase, where force is exerted to counteract the motion of the limb, instantaneous angular velocity fluctuates irregularly. But in the middle phase, angular velocity remains relatively stable. The disclosed invention, in addition to measuring and displaying relative angular position and angular displacement, obtains and displays a measurement for average angular velocity of a limb about a joint during this middle or "smooth" phase.

The device includes a brace mechanism having two pivotally connected arms worn by a patient about a limb such that at all times the angle made by the arms of the brace mechanism approximates the angle made between the joint-connected body part members of the limb.

Mounted on the brace mechanism is an angle detector which produces a signal responsive to changes in the relative angular position of the brace mechanism's arms. The output from the angle detector is inputted into a modular housing which houses the elements of a microprocessor system. Specifically, the angle detector output is inputted into a conversion means contained within the modular housing which processes signals received by the angle detector to produce a binary multi-bit output signal indicative of the relative angular position of a patient's joint-connected body part members.

Still referring to connections of elements within the modular housing, the output of the conversion means is inputted into a control means in the form of a microprocessor element. Executing transfers and transformations of data in accordance with instructions stored in a program storage means, the control means, in addition to reading the contents of the control means, writes data to and reads data from a data storage means and writes information to a display means having a screen affixed to the top of the modular housing. Further, the control means communicates with a timer means, preferably included within the microprocessor element. During performance of the invention's velocity measuring function, the control means starts and stops the timer means and reads the contents of the timer means upon stoppage. A user determines the mode of operation of the device by selecting in a predetermined fashion from a series of buttons located on top of the modular housing. The buttons are part of an input means connected to the control means.

Two modes of operation are essential for enabling the device to measure and display average angular velocity of a limb about a joint. In a first, "extremes-determination" mode of operation, a patient moves a jointed limb to a fully expanded, minimum angle position, then to a fully contracted, maximum angle position, and the angular positions associated with both extremes are stored into the device's data storage means. In a second, "velocity-determination" mode, a patient exercises a joint and the joint's average angular velocity during the middle or "smooth" phase of joint motion is measured. Average angular velocity is measured generally by starting the device's timer means upon the patient's limb reaching a predetermined position, stopping the timer means upon the limb reaching another predetermined position, reading the output of the timer means, then calculating average angular velocity by dividing degrees travelled by the output of the timer means. So that velocity irregularities characteristic of the startup and slowdown phases of motion do not affect measurement of middle phase average angular velocity, the device's program starts the timer means upon the attaining of a position far enough beyond the minimum-angle position so as to exclude data from the startup phase and stops the timer means upon the attaining of a position far enough before the maximum-angle position to exclude data from the slowdown phase. The timer means start and stop positions are preferably 15 degrees beyond the minimum position and 15 degrees before the maximum position respectively, although comparable start and stop positions will also adequately exclude startup and slowdown phase data so long as they are in the range of from about 10 to 30 degrees from the minimum and from about −10 to −30 degrees from the maximum position angles respectively.

DETAILED DESCRIPTION OF THE INVENTION

Figure 1:
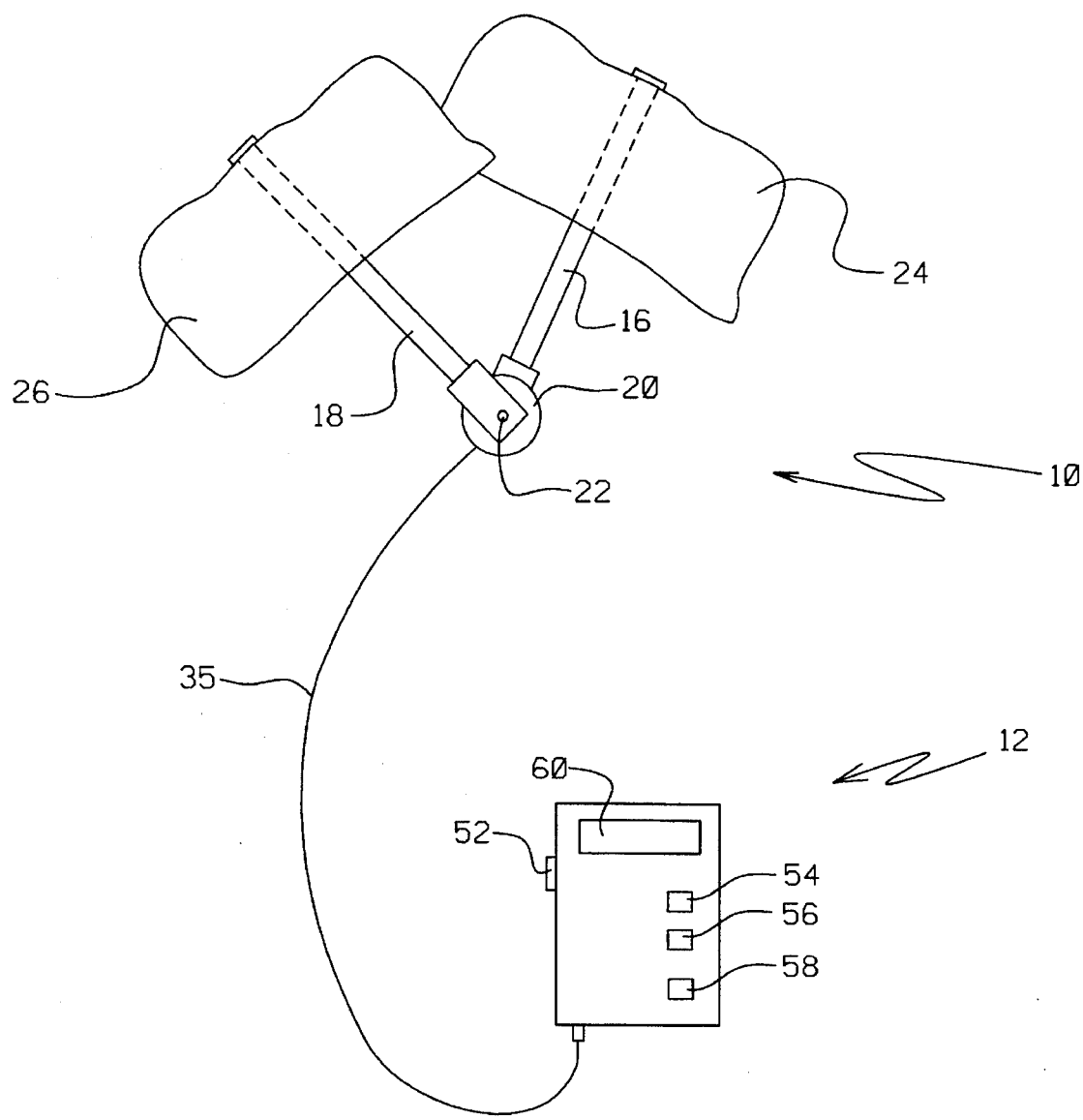
FIG. 1 shows the device, including the device's brace mechanism and its connection to the modular housing which houses the microprocessor system elements of the present invention.

Reference is now made in detail to the drawings. FIG. 1 shows a brace mechanism 10 and its connection to a modular housing 12. The brace mechanism 10 comprises two elongated rigid arms 16 and 18 pivotally connected at a pivot point. In the preferred embodiment, said pivot point is provided by a rotary-controlled angle detector 20. One of said arms 16 is fixedly attached to the fixed portion of the sensor while the other arm 18 is fixedly attached to the rotating pin 22 of the detector. Preferably, the detector 20 does not have a stopping apparatus therein stopping rotation of said rotating pin 22.

Continuing with reference to FIG. 1, the brace mechanism includes two flexible cuffs 24 and 26 attached to arms 16 and 18 respectively. In order to properly secure the brace mechanism 10 to a patient's jointed limb, one of said cuffs 24 or 26 is wrapped around and secured to one limb member while the other cuff is wrapped around and secured to the limb member connected to the joint opposite the first. For securing the cuffs to a patient's joint-connected limb members, hook-and-eye fastener (such as VELCRO) strips may be attached to the ends of the cuffs enabling attachment of the cuffs to a patient in the fashion of a standard blood-pressure measuring device. The brace mechanism is properly secured when the angle between the brace device's arms approximates, regardless of position, the angle made by the patient's joint-connected limb members. The angle detector 20 in combination with the conversion means defines a sensor means which produces a binary multi-bit signal indicative of the angle between the brace mechanism's arms. In the preferred embodiment of the sensor means, the angle detector is provided by a rotary-controlled optical encoder and the conversion means is provided by a counter. In an alternative embodiment of the sensor means, the angle detector is provided by a rotary-controlled potentiometer and the conversion means is provided by an analog-to-digital converter. In another embodiment of the sensor means, the angle detector is provided by a rotary-controlled piezoelectric device and the conversion means is provided by an analog-to-digital converter.

With further reference to FIG. 1, flexible conduit 35 carries the output from the angle detector 20 to the modular housing 12, where it is connected within the housing to a conversion means (connection not shown).

Mounted to the exterior of the modular housing 12 are a plurality of buttons including a power button 52 which causes power to be supplied to the electronic elements of the device housed within the modular housing, and three control buttons 54, 56, and 58. Primarily, buttons 54 and 56, designated as "Function/Data Scroll" buttons are used to toggle between menu options representative of different modes of operation of the device, while button 58, designated as the "Function Select/Data Acquire" button is used select one of said options and transfer program control to the selected mode of operation. During the "extremes-determination" mode of operation the "Function Select/Data Acquire" button is used to cause storage of data pertaining to minimum and maximum relative angular position and to cause branching of program control to the "velocity-determination" mode of operation.

Further mounted to the modular housing 12 is a display screen 60, preferably an LCD screen. The display screen will display various information to the user depending on the particular mode of operation of the device. Such information may include information related to menu choice options, relative angular position of the arms of the brace mechanism 10, average angular velocity of moving limb members about a joint, or angular displacement of a limb about a joint.

Figure 2:
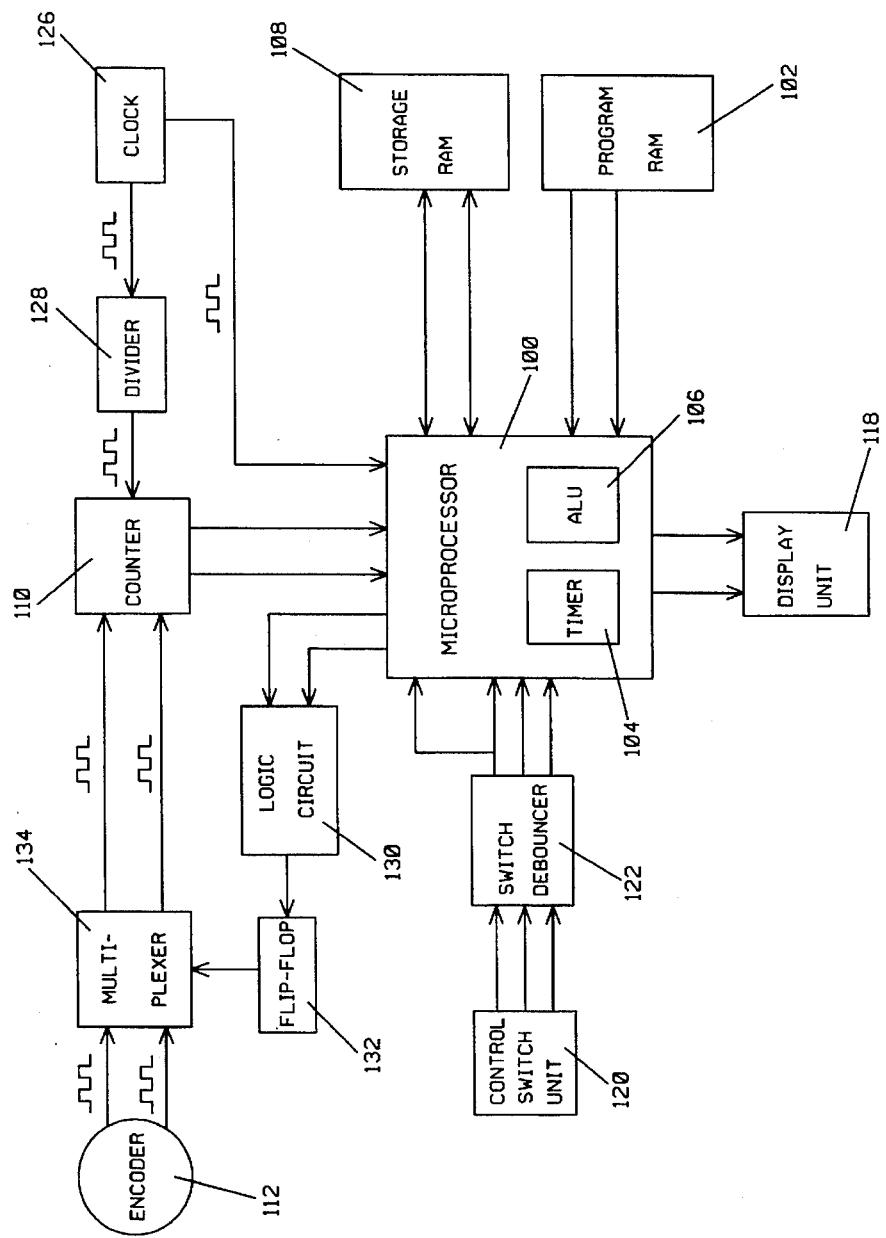
FIG. 2 shows a block diagram of inputs and outputs in a representative microprocessor for the present invention.

Reference is now made specifically to FIG. 2 of the drawings wherein a general and specific description of the internal electronics of the invention will be made. The heart of the present invention is the microprocessor 100, which controls and synchronizes data transfers and transformations in accordance with instructions stored in and read from the program ROM 102. The microprocessor comprises several subunits that are not shown for clarity purposes including a control unit having a program counter and a plurality of internal registers which temporarily store data as the microprocessor executes logic operations or mathematical computations. Two subunits of the microprocessor that are shown in FIG. 2 are the timer 104, which responds to timer start and stop instructions during the invention's velocity-determination mode of operation enabling the microprocessor to record the elapsed time between execution of said timer start and stop instructions and the arithmetic logic unit (ALU) 106, the microprocessor subunit which performs logic operations and mathematical computations on data temporarily held within the microprocessor's internal registers.

Still referring to FIG. 2, the microprocessor 100 communicates with an external read-write memory unit, the storage RAM 108. The storage RAM stores recallable data on a temporary basis during the performance of certain data transformation routines, and can also store recallable data permanently or on a long-term basis for filing purposes when a user wishes to store completed measurements for future reference. Not shown in FIG. 2 but an element of the preferred embodiment of the present invention is a battery unit connected to said storage RAM 108, which enables the RAM to continually store data when the microprocessor system is powered down.

When a patient moves a joint during the invention's "extremes-determination" mode of operation, or exercises a joint during the invention's velocity-determination mode of operation, the microprocessor reads data indicative of the relative angular position between two body part members from the angle-increment counter 110. The angle-increment counter works in combination with the preferred angle detector of the present invention, the optical encoder 112 (described generically in FIG. 1 as an angle detector 20), to produce a binary multi-bit signal proportional to the angle between the body part members of a patient wearing the previously described brace device. As a joint is moved (during the "extremes-determination" mode) or exercised (during the "velocity-determination" mode), the optical encoder produces two binary pulse signals, A and B, which are 90 degrees apart. During measurement of angular velocity with the pin-mounted arm 18 (FIG. 1) moving in a clockwise direction with respect to the fixed arm member 16 (FIG. 1), expanded-to-contracted position joint movement causes the A signal to lead B, while contracted-to-expanded position joint movement causes the B signal to lead A. These pulse signals are inputted to the counter 110 which increments an internal register when it receives an A before B pair of pulses, and decrements said internal register when it receives a B before A pair of pulses. The counter 110 produces a binary multi-bit output signal indicative of the current angle between the arms of the brace mechanism.

The preferred embodiment of the present invention's angle sensor means further includes switching hardware for switching of the sensor means from a first mode enabling the sensor means to increment during clockwise rotation of the brace mechanism 10 (FIG. 1.), to a second mode enabling the sensor means to increment during counter-clockwise brace mechanism rotation.

It is understood with reference again to FIG. 1 that such switching means enables the device to be worn in a fashion that is maximally comfortable and minimally encumbering to natural joint movement. Since the angle detector 20 typically has a substantial thickness of about an inch, and the pin 22 protrudes outwardly only a few centimeters, it is preferred that the brace mechanism 10 be worn such that the detector points outwardly from the outside of a patient's joint so that the mechanism minimally encumbers natural joint movement. It can be seen that if upper cuff 24 is properly worn on the upper limb member of a patient's right arm, and lower cuff 26 on the patient's lower right arm, then pin-mounted arm 18 will rotate clockwise with respect to fixed arm 16 as a patient moves his or her joint from an expanded to a contracted position. However, if the brace mechanism is worn on a patient's left arm, with upper cuff 24 properly worn on the limb's upper member and lower cuff 26 on the limb's lower member with detector 20 properly pointing outwardly, then pin-mounted arm 18 will rotate counterclockwise with respect to fixed arm 16 as a patient moves his or her joint from an expanded to contracted position. Although transferring the lower cuff 26 to a patient's upper limb member and the upper cuff 24 to patient's lower limb member for left arm angular velocity measuring would result in clockwise rotation of the brace mechanism, the measuring technique is not preferred since upper cuff 24 preferably is especially well-suited for wear on an upper limb member and lower cuff 26 is especially well-suited for wear on a lower limb member. It is understood that pivoting arm 18 will move generally clockwise during left leg velocity measuring and counter-clockwise during right leg velocity measuring.

Now referring to specific elements of the switching means, shown in FIG. 2 is a logic circuit 130, tied to at least a portion of the system's address bus, having typically 8 inputs and a single output. When one specific control address is accessed (typically having a sequence of 11111111) by the microprocessor, the output of the logic circuit turns high. The output from the logic circuit 130 in turn is inputted into a flip flop 132, the output value of which changes signs each time said control address is accessed.

Continuing with reference to FIG. 2, the output from the flip flop 132 is inputted into a multiplexer 134 as are the pair of binary output signals from the encoder 112. When the signal from the flip flop is low (corresponding to clockwise movement of the brace mechanism) the output from the multiplexer, inputted into the counter 110, will be the same as that from the encoder, a pair of binary pulse signals with the A signal leading the B signal by 90 degrees. However, when the control address is accessed the output signals from the multiplexer 134 will be reversed and the B signal will lead the A signal by 90 degrees. The switching hardware enables the counter 110 to count upward on command whether the pin-mounted arm of the brace mechanism 18 (FIG. 1) is moved clockwise with respect to the fixed arm member 16 (FIG. 1) or counterclockwise.

In addition to enabling the brace mechanism 10 (FIG. 1) to be worn on any limb of a patient in a fashion that is most comfortable and least encumbering to natural joint movement, the multiplexer switching means described above enables the device to easily measure angular velocity in reverse-direction. The device is intended to be used to measure average angular velocity primarily in the direction of expanded-position to contracted-position joint movement. Normally, before being fitted to a patient's limb, the brace mechanism is laid on flat surface with arms 16 and 18 fully expanded forming a straight line, whereupon the device's power is turned on. In this way (with the encoder-counter embodiment of the invention) an angle reference is created with an angle of zero corresponding to the fully expanded arm position. Assuming right arm or left leg measuring, clockwise rotation of the mechanism causes the counter output to increment. It is easily seen how the multiplexer switching means enables bi-directional measuring of angular velocity. For reverse-direction measuring (from a contracted limb position to an expanded one) the first step again is creating a reference angle. Rather than expanding the arms of the brace mechanism, however, the arms are fully contracted such that the pivoting arm 18 lies directly over the fixed arm 16, whereupon the device power is turned on. With the zero angle referenced to correspond to the fully contracted position, reverse-direction measuring may be accomplished simply by activating the control signal into the multiplexer (again assuming right arm or left leg measuring) such that the counter counts upward upon counter-clockwise brace mechanism rotation.

While the encoder-counter combination exhibits numerous advantages in that it is accurate, fast, allows flexibility of measuring techniques, and does not require calibration, other combinations of devices will also satisfactorily indicate body part member angular position. Specifically, a rotary variable resistor (with voltage source), a rotary piezoelectric device, or any other rotary-controlled device producing a DC voltage varying linearly with the angular position of the rotary encoder of said device in combination with an analog-to-digital converter will also produce, at the output of said analog-to-digital converter a multi-bit binary signal indicative of angular displacement.

Importantly however, certain hardware and software elements of the present invention necessary for supporting the invention's angular displacement sensing function will vary depending on the particular sensor means implemented.

In particular, with reference to FIG. 2, if the optical encoder and counter combination is used, the output from the clock 126 will be inputted both to the microprocessor 100 and to a divider 128 whose output in turn, is inputted into the counter 110. If however the combination of a rotary-controlled, DC voltage producing device with an analog-to-digital converter is implemented, the output from the clock 126 is simply inputted into the microprocessor 100 (embodiment not shown).

Another hardware element whose embodiment will vary depending on the chosen angle sensor means is the multiplexer 134 described above in detail. If a potentiometer is used in combination with an A/D converter instead of the encoder-counter combination, for example, the digital multiplexer, capable of reversing the encoder's signals must be replaced with an analog switch (still activated by the microprocessor's control signal) capable of reversing the potentiometer's positive and ground terminals.

Referring now to software elements that vary depending on the sensor means chosen, it is understood foremost that implementation of an embodiment of the present invention including an analog-to-digital converter will require that the device's program include several instructions during various modes of operation of said device for controlling conversions performed by said analog-to-digital converter.

In addition, software elements scaling the output of the invention's sensor means will vary depending on the sensor means chosen. With reference to FIG. 2, it is understood that the output of the counter 110 is a value that is merely indicative of the angle between the brace mechanism's arms and is not equal to the actual angle between said arms. More specifically, the output of the counter is a value inversely proportional to the angle between the arms where the zero angle is referenced at the fully-expanded arm position, and directly proportional where the zero angle is referenced at the contracted position. Since the value of the counter output is proportional (inversely or directly) to the actual angle between the brace's arms the output must be scaled to represent actual angular position.

In the inventors' embodiment, a counter is used that increments 512 times per 360 degree revolution of the encoder. Therefore, whenever during the course of operation of the device the microprocessor reads the counter output, that output must be multiplied by $360/512=0.703125$ in order for that value to represent actual angular position. Obviously, the scaling multiplier must be changed as different angle detectors are implemented. Use of a potentiometer producing an output voltage increasing from 0 to 7 volts per 360 degree revolution, for example, would require a scaling multiplier of $360/7=51.43$.

Continuing with reference to FIG. 2, also connected to the microprocessor 100 is a display unit 118. Depending on the mode of operation of the present invention, the microprocessor will write various data to the display unit. These data may be in the form of messages read from the program ROM related to menu options, or may involve data read by the microprocessor from the angle-increment counter, or transformed data from the microprocessor related to angular displacement or velocity.

Further shown in FIG. 2 is a control switch unit 120 which enables switching of the device to different modes of operation. In the preferred embodiment of the present invention, three buttons are included within the control switch unit. The outputs from these buttons are inputted into a switch debouncer 122 and in turn, inputted into a reserved port of the microprocessor. Preferably, one of said buttons, designated as the "Function Select/Data Acquire" button 58 (FIG. 1) is tied to an interrupt pin of the microprocessor 100 such that depression of the "Function Select/Data Acquire" button generates a hardware interrupt of the program's present routine except where the hardware interrupt function is disabled. Generally, where the microprocessor's hardware interrupt function is disabled, the "Function Select/Data Acquire" button, along with the other two "Function/Data Scroll" control buttons 54 and 56 are used for generating software interrupts of the program's present routine. At several different stages of the program of the device, the control signals received in the microprocessor reserved port are redundantly interrogated. Branching of program control of the present invention depends generally on the particular control button depressed and the status of additional flags, representing the current mode of operation of the device, which are also interrogated.

Figure 3:
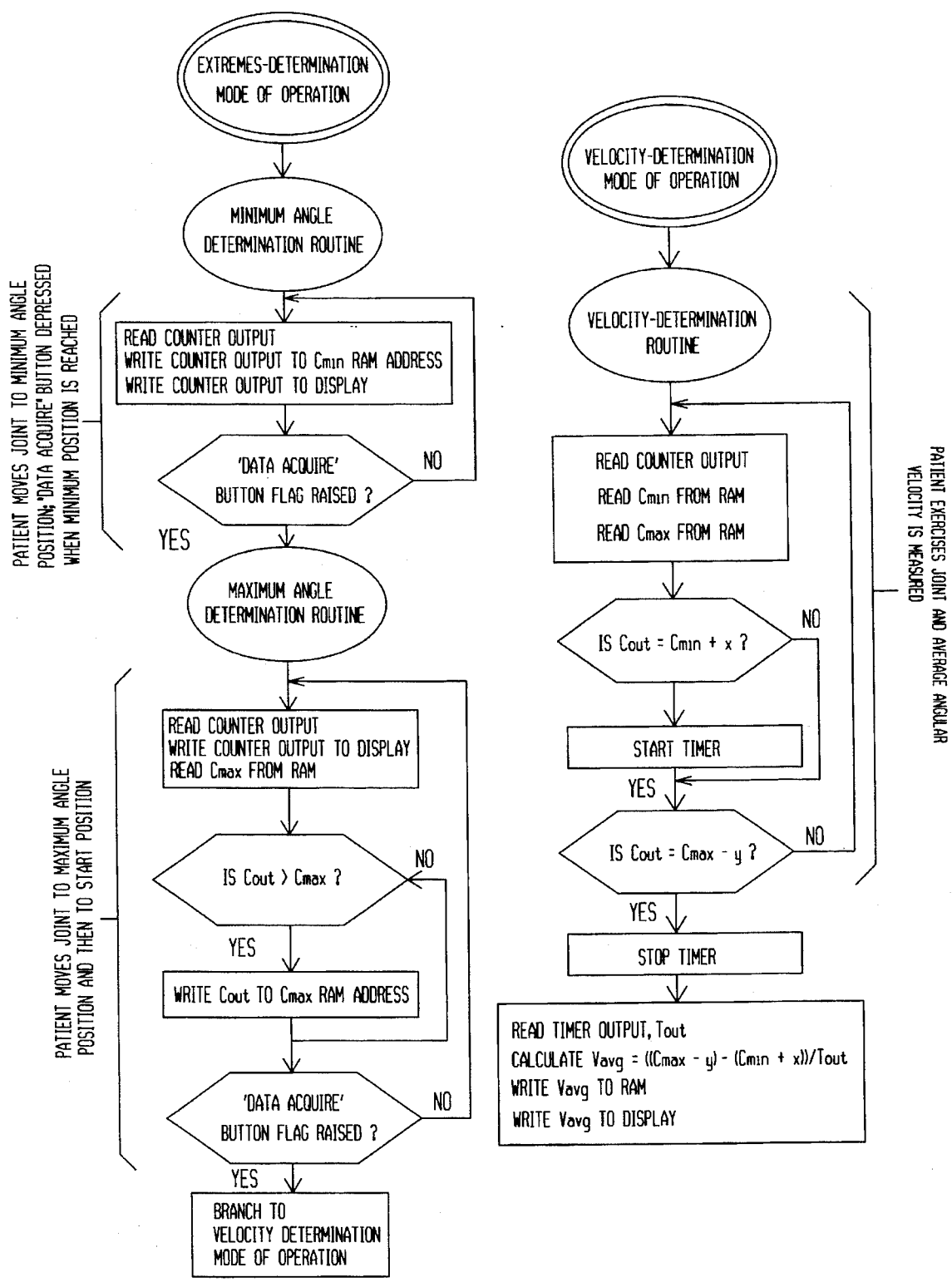
FIG. 3 shows a flow diagram of representative program routines enabling the device to measure and display average angular velocity of a moving joint while a patient moves and exercises a joint in accordance with a prespecified routine.

The discussion will now be expanded to include reference to FIG. 3, showing a flow diagram of the computer program routines enabling the present invention to measure and display average angular velocity of a moving joint. By describing the transfers of data between the invention's microprocessor system elements and transformations of data within the microprocessor itself during execution of the set of instructions represented in the flow diagram of FIG. 3, design requirements of the invention's computer hardware and software elements will become clear to the person skilled in the art wishing to make the present invention. When the system is powered up, program control defaults to the "extremes-determination" mode of operation depicted at the left side of FIG. 3. At the start of the routine, the microprocessor 100 continually reads data from the angle-increment counter output 110 (and scales that output), writes the data to a specified address of the storage RAM 108 designated as the minimum-angle address, and writes the data to the display unit 118, providing a continuous readout representative of the current angle between two body part members of the subject patient. During this stage of the routine, the patient attempts to move his or her joint to a minimum-angle, fully expanded position. The process of reading the output of the angle-increment counter, storing this data at a specified address, and displaying the counter output continues until the patient's joint reaches a minimum-angle, fully expanded position, at which point the user depresses the "Data-Acquire" button generating a interrupt signal. The last counter output value stored in RAM at the specified minimum angle address before reception of the interrupt signal will be maintained as the value for minimum angle of displacement. If the routine is designed to terminate upon reception of a hardware interrupt, program control temporarily transfers to the program's interrupt routine. During execution of the interrupt routine, flags representing the device's present mode of operation are interrogated whereupon the program, continuing with the "extremes determination" mode of device operation, branches to a routine for determining maximum angle. If the minimum angle routine disables the microprocessor's hardware interrupt function, branching of the program to the maximum angle routine is instead controlled, as is illustrated in the drawing, by way of redundant interrogation of the "Function Select/Data Acquire" signal at the reserved port of the microprocessor.

When program control branches to the maximum-angle determination routine, a patient attempts to contract his or her joint to a maximum angle position while the microprocessor 100 once again reads data from the counter output and writes the output to the display unit. But instead of continually writing the counter output to a specified RAM address as a preliminary value for maximum angle of deflection, the microprocessor reads a pre-set value for maximum deflection angle from the RAM (initially set to 0) and the microprocessor's ALU 106 compares this value to the current counter output. Only if the current counter output is greater than the previous value for maximum deflection angle retrieved from RAM will that maximum angle RAM address be overwritten.

The routine is programmed as such because it is expected that a patient might want to "warm up" after the extremes of her joint movement are recorded but before the velocity of her joint is measured. The described routine allows a patient to make practice flexings or exercises of her joint in preparation of a "real" flexing during which she will typically attempt to move her joint with maximum possible velocity.

After a patient performs such practice flexings, or after she simply moves her joint to a comfortable starting position, both the device and the patient are prepared for joint velocity measuring. To activate measuring, the "Function Select/Data Acquire" button is depressed to generate an interrupt (hardware or software) and program control branches to the "velocity-determination" mode of operation represented by the flow diagram on the right side of FIG. 3. At the start of the velocity-determination mode of operation, comprising a single velocity-determination routine, the microprocessor 100 reads the values for maximum and minimum angles previously stored in Ram during the extremes-determination mode of operation, then the microprocessor's ALU 106 adds to the value for minimum angle a value of x degrees (read from the program ROM 102) and subtracts from the value for maximum angle a value of y degrees (also read from the program ROM 102), creating new variables which are designated in the flow diagram as Aon and Aoff. The values for Aon and Aoff are then stored in internal microprocessor registers. In the preferred embodiment the values of x and y are both set to 15 degrees although similar values for x and y will also enable reliable measurement of average angular velocity so long as both are in the range of from about 10 degrees to 30 degrees.

The microprocessor then reads the counter output and the microprocessor's ALU 106 compares the counter output value first to the value for Aon, then to the value for Aoff. As the patient exercises his or her joint during the velocity-determination routine to continually increment the counter, the microprocessor will activate an internal timer 125 upon the condition that the counter output equals Aon and will stop said timer upon the condition that the counter output equals Aoff. The microprocessor's internal timer 104 counts down upon activation and overflows within a microsecond. Since the timer typically will overflow several times between start and stop signals, an internal register is included in the preferred embodiment which increments upon overflow to keep a running track of the total number of overflows occurring between reception of timer start and stop signals. When a timer stop instruction is encountered upon the condition that the counter output equals Aoff, the microprocessor will stop the timer 104 then read the contents of both the timer overflow register and the timer to arrive at a value for Tout, the total time between execution of timer stop and start instructions. The microprocessor's ALU 106 then calculates average angular velocity by dividing the difference between Aon and Aoff by Tout. Average angular velocity is then written to a specified Ram address and written to the display unit 118.

In addition to the set of instructions represented in the flow diagram of FIG. 3, which enable the device to measure average angular velocity while a joint is moved and exercised in a prespecified manner, the preferred software of the present invention includes program routines enabling the present device to perform various other functions. These additional routines include setup routines, a routine for calculating angular displacement, and data filing routines.

The most frequently accessed setup routine is likely to be the "change-rotation" routine. As mentioned, when the device is powered up, program control defaults to the "extremes-determination" mode of operation depicted on the left side of the flow diagram of FIG. 3. When the default routine is accessed the device will be set up to measure brace mechanism movement in the direction of the last-performed measurement. More specifically, if for example the brace mechanism rotated clockwise during the last attained velocity measurement, the output of the flip flop 132 (FIG. 2) will be low, causing the counter to increment upon clockwise brace mechanism rotation. From what has been discussed it is understood that if the new measurement to be performed involves a different limb not diagonal from the last-measured limb, or is a reverse-direction measurement, the output value of the flip flop 132 must be changed. To change the flip flop output, the first step is to depress one of the "Function/Data Scroll" control buttons. The minimum-angle determination routine of the program includes instructions causing redundant interrogation of the microprocessor's reserved control input port such that depression of one the "Function/Data Scroll" buttons causes branching of the program to a menu routine. Within the menu routine, further depression of one of the "Function/Data Scroll" buttons causes messages indicative of menu choice options to appear on the display screen. When the proper "rotation-change" menu choice appears, the user depresses the "Function Select/Data Acquire" button to activate the routine. The rotation-change routine consists simply an instruction wherein the control address activating the logic circuit 130 (and therefore the flip flop) is read or written to.

Another setup routine is the "initial angle" routine. As mentioned, the initial angle is normally zero and is referenced by fully expanding the arms of the brace mechanism until they form a straight line before turning the device on. Certain applications however require that the initial angle be referenced at a value other than zero. For example, the velocity of a knee joint is often measured by fitting the brace mechanism on a patient in a sitting position and the initial angle preferably is referenced at 90 degrees (the brace is applied across a right angle template before the setup routine is accessed). In addition, where a user wishes the device to produce values of actual relative angular position of the brace mechanism's arms and not complementary-angle values, the initial angle may be referenced at 180 degrees. For changing the initial angle the menu routine is once again accessed and one or the other of the "Function/Data Scroll" buttons is depressed until a message indicating the "initial angle" routine appears. Subsequent depression of the "Function Select/Data Acquire" buttons causes a sub-menu to appear indicating the zero, 90, and 180 degree options. Accessing the 90 or 180 degree options causes the chosen initial angle value to be added to the scaled counter output each time data is read from the counter.

Discussion of the device's motion characteristic measurement capabilities has been limited thusfar to its ability to measure and display relative angular position between the arms of the brace mechanism and its ability to measure average angular velocity. In addition to these measuring capabilities, the device may be easily programmed to measure and display angular displacement, the distance in degrees between the minimum and maximum attained angles. For enabling this and other functions, the program's "velocity-determination" routine includes instructions such that the menu routine may be accessed after average angular velocity is displayed. When the menu is accessed and the "angular displacement" routine is accessed from the menu, the microprocessor 100 (FIG. 2) reads data from the minimum and maximum angle address locations of the storage RAM 108, the microprocessor's ALU 106 calculates the difference between maximum and minimum angles, and the microprocessor writes the resulting value for angular displacement to the display unit 118.

Further included in the preferred software is a "file data" routine, also appearing as a menu option. At the start of the "file data" routine, the program requests information regarding identification of the patient and the date of the measurement. Such information may be entered by depressing the "Function/Data Scroll" control buttons to scroll through letters of the alphabet, years, months or days, then depressing the "Function Select/Data Acquire" when the desired letter, year, month or day is displayed. Once the patient identification information is entered, the microprocessor reads data from address locations of the storage RAM 108 (FIG. 2) corresponding to last-obtained values for minimum and maximum relative position angles, average angular velocity, and possibly angular displacement and writes this data to new address locations of the storage RAM which are identifiable according to the inputted patient identification information.

Of course, having a routine for filing data would be useless if the data could not be recovered at a later time. Accordingly, the preferred software includes a "review data" routine enabling recovery of previously stored data. Unlike the "angular displacement" and "file data" routines which perform useful functions only after a successful angular velocity measuring routine is completed, the "review data" routine may be properly accessed at any time during the course of operation of the device, even before an angular velocity measuring cycle is begun.

Commonly, a user will use the disclosed device only to review previously stored data without intending to perform any measurements. To accomplish such data review, the system is powered up and, in the same way the setup routines are accessed, one of the "Function/Data Scroll" buttons is depressed to branch the program from the minimum angle routine to the menu routine. When the "review data" menu option is selected, the prompts for information regarding the identification of the patient, and the microprocessor reads previously stored data by addressing the storage RAM 108 (FIG. 2) based on the inputted patient identification information. The data read from the storage RAM is then written to the display unit. The "Function/Data Scroll" control buttons may be used to scroll through, in sequential order, data related to minimum angular position, maximum angular position, average angular velocity, and angular displacement.

Although the present invention has hereinabove been described with great particularity, it is understood that various modifications, changes and alterations in the teachings of the present invention may be made by those skilled in the art without departing from the intended scope and spirit thereof. Accordingly, it is to be stressed that it is intended that the present invention be limited only by the terms of the appended claims.

A printout of the computer program listing, written in C, used by the inventors in their embodiment of the present invention is presented on the following pages.

```c
/******************* Angular Velocity Computer *********************/ include <io51.h> define UP 3
define DOWN 5
#define ENTER 6
#define TRUE 1
#define FALSE 0
#define Equals ==
#define NotEquals !=
#define Or ||
define And && struct subject
  {
    char  name[10];
    float trial[10];
    int   StartDeg,EndDeg;
    char  TrialCounter;
  };

pragma memory = no_init char StartPos,      /* starting position of encoder in degrees */
      Rot,            /* contains 1 or 0 for cw or ccw motion */
      CurrentSub,     /* contains the current subject number */
      SubCounter,     /* contains the total number of subjects in the dbase */
      IDCounter,      /* contains the number of letters in subject name */
      NotFirstEntry;  /* defaults to a 0 cause first power on is not first entry
*/
  struct subject SUB[5];

#pragma memory = default
/***********************************************************************
          OVERHEAD AREA (TIMER/SOFTWARE CALIBRATION)
 ***********************************************************************/ char TIMEHIGH = 0xFC,  /* <--- This is the high value */
     TIMELOW  = 0x3F;  /* <--- This is the low value */ long TIMEINT =0xFC3F; /* This is the high and low togther */

/* IF YOU CHANGE EITHER THE TIMEHIGH OR THE TIMELOW, YOU MUST ALSO CHANGE
   THE TIMEINT SO THEY ALL MATCH
*/

/*  ABOVE EXAMPLE: FFFF    (65535)
              -   3E8    (1000)   <--- 1000 INT OVERFLOW -DON'T CHANGE !
```

```
                 -------------------
                 FC17      (64535)
            +     28         (40)     <---- OVERHEAD - YOU CHANGE THIS
                 -------------------
                 FC3F       64575
*/
/*******************************************************************/ long time1 = 0,temp,num;

int StartMenu,EndMenu,      /* used for overall display, not just the menus */
    DecPart,                /* decimal part of a value to be displayed */
    CurDeg,
    OldDeg,                 /* used for powering down */

TimeHigh1,TimeLow1,
    TimeHigh2,TimeLow2,
    NewStart,NewEnd,
    PosOffset,              /* offset for rotary encoder */
    loop,                   /* global loop counter */
    RetStart   = 254,RetEnd   = 270,
    CCStart    = 270, CCEnd   = 302,
    ChPosStart = 302, ChPosEnd = 350;

char KeyRead,ButtonDown,CurrentTrial,
     test1,test2,OldKey,RUPT = 0,
     set1,set2,set3,
     MenuStart   = 14 ,MenuEnd  = 94,
     SetUpStart  = 94, SetUpEnd = 174,
     IDStart     = 174,IDEnd    = 190,
     NewNum      = 238,OldNum   = 254,
     ReviewStart = 174,ReviewEnd = 238;

char message[366]=
  {
    83,84,65,82,84,                                  /* START           */
    65,78,71,32,86,69,76,61,32,                      /* ANG VEL=        */

/* Main Menu */

67,79,78,84,73,78,85,69,32,32,32,32,32,32,32,32, /* CONTINUE        */
    83,69,84,32,85,80,32,32,32,32,32,32,32,32,32,32, /* SET UP          */
    68,79,87,78,76,79,65,68,32,68,65,84,65,32,32,32, /* DOWNLOAD DATA   */
    82,69,86,73,69,87,32,68,65,84,65,32,32,32,32,32, /* REVIEW DATA     */
    68,69,76,32,76,65,83,84,32,69,78,84,82,89,32,32, /* DEL LAST ENTRY  */

/* Set-Up Menu */

69,78,84,69,82,32,83,85,66,74,69,67,84,32,73,68, /* ENTER SUBJECT ID */
    67,72,65,78,71,69,32,83,84,65,82,84,32,80,79,83, /* CHANGE START POS */
    67,72,65,78,71,69,32,82,79,84,65,84,73,79,78,32, /* CHANGE ROTATION  */
```

```
      67,76,69,65,78,32,68,65,84,65,66,65,83,69,32,32, /* CLEAN DATABASE  */
      69,88,73,84,32,83,69,84,32,85,80,32,32,32,32,32, /* EXIT SET UP     */

/*  Review Menu */

83,85,66,32,73,68,32,32,32,32,32,32,32,32,32,32, /* SUB ID          */
      77,73,78,32,65,78,71,61,32,32,32,32,32,32,32,32, /* MIN ANG=        */
      77,65,88,32,65,78,71,61,32,32,32,32,32,32,32,32, /* MAX ANG=        */
      84,82,73,65,76,32,35,32,32,32,32,32,32,32,32,32, /* TRIAL #         */

/* Enter Sub Id submenu */

40,78,41,69,87,32,47,32,40,79,41,76,68,63,32,32, /* (N)EW / (O)LD?  */
      82,69,84,32,73,68,32,32,32,32,32,32,32,32,32,32, /* RET ID          */

/* Direction Submenu */

67,79,85,78,84,69,82,67,76,79,67,75,87,73,83,69, /* COUNTERCLOCKWISE */
      67,76,79,67,75,87,73,83,69,32,32,32,32,32,32,32, /* CLOCKWISE       */

/* Rotational Submenu */

83,84,65,82,84,32,80,79,83,32,61,32,32,32,48,223,/* START POS =   0^ */
      83,84,65,82,84,32,80,79,83,32,61,32,32,57,48,223,/* START POS =  90^ */
      83,84,65,82,84,32,80,79,83,32,61,32,49,56,48,223,/* START POS = 180^ */

/* Battery Low message */
      66,65,84,84,69,82,89,32,76,79,87,32,32,32,32,32
    };

void WaitTillReady()
{
  char loop;

loop = ((char *)0x010000)[0xE002];
  while (loop >= 128)
    loop = ((char *)0x010000)[0xE002];
} void PrintMessage(StartMark,EndMark)
int StartMark,EndMark;
{
  int loop1;

WaitTillReady();((char *)0x010000)[0xE000] = 0x80;
  for (loop1 = StartMark;loop1 < EndMark;loop1++)
     {
       if (loop1 Equals (StartMark + 8))  /* if cursor is ready for next display */
       {
         WaitTillReady();((char *)0x010000)[0xE000] = 0xC0;
```

```
      }
       WaitTillReady();
       ((char *)0x010000)[0xE001] = message[loop1];
     }
} void ClearScreen()
{
  WaitTillReady();((char *)0x010000)[0xE000] = 0x01;
  WaitTillReady();((char *)0x010000)[0xE000] = 0xC0;
  WaitTillReady();((char *)0x010000)[0xE000] = 0x01;
} void SetBits()
{
  WaitTillReady();

ET0=IT1=EA=1;

((char *)0x010000)[0xE000] = 0x0C;
  ((char *)0x010000)[0xE008] = Rot;

TMOD=1;

TH0=TIMEHIGH;
  TL0=TIMELOW;

TR0=1;
  PX1=1;

if (StartPos Equals 180)
     PosOffset=0;
  else if (StartPos Equals 90) PosOffset=270;
  else PosOffset=180;
} int ReadPort()
{
  char oddcheck;
  int Degrees;

oddcheck = ((char *)0x010000)[0xE004];
  Degrees =  ((char *)0x010000)[0xE005];

Degrees = (int)(Degrees*.703125);

if (oddcheck%2 Equals FALSE) Degrees+=StartPos;    /* if even add 90 */
```

```
    else
      {
      Degrees+=PosOffset;                          /* otherwise subtract 90 */
      if (Degrees > 360) Degrees-=360;
      };
  return(Degrees);
} void Display(Deg)
char Deg;
{
  int num;
  char DecFlag;

if (CurDeg <= 100.0)
    DecFlag = TRUE;
  else DecFlag = FALSE;

WaitTillReady();((char *)0x010000)[0xE000] = 0x89; /* 89 */
  WaitTillReady();((char *)0x010000)[0xE000] = 0x38;
  WaitTillReady();((char *)0x010000)[0xE000] = 0xC1;

num = (int) (CurDeg / 100);
  CurDeg -= num*100;
  WaitTillReady();((char *)0x010000)[0xE001] = num+48;

num = (int) (CurDeg/10);
  CurDeg-= num*10;
  WaitTillReady();((char *)0x010000)[0xE001] = num+48;
  WaitTillReady();((char *)0x010000)[0xE001] = (int) CurDeg+48;

if ( (Deg Equals TRUE) && (DecFlag Equals TRUE ))  /* display the decimal */
    {
      WaitTillReady();((char *)0x010000)[0xE001] = 0x2E;
      num =(int) DecPart / 10;
      DecPart-=num*10;
      WaitTillReady();((char *)0x010000)[0xE001] = num + 48;
      WaitTillReady();((char *)0x010000)[0xE001] = (int) DecPart + 48;
    }
  WaitTillReady();((char *)0x010000)[0xE001] = 0xDF;
  if ( (DecFlag Equals FALSE) && (Deg Equals TRUE) )
    {
      WaitTillReady();((char *)0x010000)[0xE001] = 0x2F;
      WaitTillReady();((char *)0x010000)[0xE001] = 83;
    }
}

/**************** INTERUPT AREA ******************************/ pragma function=interrupt
```

```c
void T0_int (void)
{
  char loop;

TH0=TIMEHIGH;
  TL0=TIMELOW;

time1++;
} void EX1_int (void)        /* used for button press when powered down */
{
  char loop;
  int loop1;

KeyRead = P1;KeyRead = KeyRead & 8;
    {
      ButtonDown=TRUE;OldKey=ENTER;
      loop = ((char *)0x010000)[0xE002];
      while (loop >= 128)
     loop = ((char *)0x010000)[0xE002];
      ((char *)0x010000)[0xE000] = 0x0C;
      KeyRead = P1;KeyRead = KeyRead & 7;
      while (KeyRead NotEquals 7)
    {
      KeyRead = P1;KeyRead = KeyRead & 7;
    }
      ET0 = 1;EX1 = 0;
    }
} pragma function = default

/*******************************************************************/ void SendOver(Deg)
char Deg;
{
  int loop1;

num = (int) (CurDeg / 100);
  CurDeg -= num*100;SBUF = num+48;
  for (loop1=0;loop1<10000;loop1++)
    {
    } num = (int) (CurDeg/10);
  CurDeg-= num*10;SBUF = num+48;
  for (loop1=0;loop1<10000;loop1++)
    {}
```

```
   SBUF = (int) CurDeg+48;
   for (loop1=0;loop1<10000;loop1++)
     {} if (Deg Equals TRUE)                          /* display the decimal */
     {
       SBUF = 0x2E;
       for (loop1=0;loop1<10000;loop1++)
         {} num =(int) DecPart / 10;
       DecPart-=num*10;SBUF = num + 48;
       for (loop1=0;loop1<10000;loop1++)
         {}

SBUF = (int) DecPart + 48;
       for (loop1=0;loop1<10000;loop1++)
         {}
     }
} void DownloadData()
{
/* Download parameters to be determined by host computer requirements and
   statistical software.*/
} void ReviewUp(StartMenuValue,MaxEndMenu)
char StartMenuValue,MaxEndMenu;
{
   if (StartMenu Equals StartMenuValue) /* Wrap-around effect */
     {
       if (SUB[CurrentSub].TrialCounter NotEquals 0)
       {
         CurrentTrial=SUB[CurrentSub].TrialCounter;
         StartMenu=MaxEndMenu;
       }
       else StartMenu=MaxEndMenu-16;
     }
   else if (CurrentTrial Equals 1)
     {
       StartMenu=(ReviewEnd-16);CurrentTrial=0;
     }
   else if (CurrentTrial > 0)
     {
       StartMenu=EndMenu;   /* This will force no change */
       CurrentTrial--;
     }
}
```

```
void ReviewDown(StartMenuValue,MaxEndMenu)
int StartMenuValue,MaxEndMenu;
{
  if (EndMenu Equals MaxEndMenu)
    {
       if ( (CurrentTrial Equals SUB[CurrentSub].TrialCounter) Or
         (SUB[CurrentSub].TrialCounter Equals 0) )
      {
        CurrentTrial=0;
        EndMenu=StartMenuValue;
      }
       else
      {
        CurrentTrial++;
        EndMenu=StartMenu;
      }
    }
  else if ( (EndMenu Equals MaxEndMenu-16) And
        (SUB[CurrentSub].TrialCounter Equals 0) )
    EndMenu = StartMenuValue;
} void MenuUp(StartMenuValue,MaxEndMenu)  /* used for menu and changing starting */
int StartMenuValue,MaxEndMenu;          /* positions */
{
  if (StartMenu  Equals  StartMenuValue) /* Wrap-around effect */
    StartMenu=MaxEndMenu;
} void MenuDown(StartMenuValue,MaxEndMenu) /* used for menu and changing starting
*/
int StartMenuValue,MaxEndMenu;              /* positions */
{
  if (EndMenu  Equals  MaxEndMenu) /* Wrap-around effect */
    {
       if ( (StartMenuValue  Equals  MenuStart) Or
          (StartMenuValue Equals SetUpStart) Or
          (StartMenuValue Equals ChPosStart) Or
          (StartMenuValue Equals CCStart) )
       EndMenu=StartMenuValue;
    }
} char LetterDown(LetterToDisplay)
char LetterToDisplay;
{
  EndMenu=StartMenu;
  if (LetterToDisplay  Equals   42) LetterToDisplay=127;
    else if (LetterToDisplay  Equals   65) LetterToDisplay=42;
```

```
      else if (LetterToDisplay  Equals  48) LetterToDisplay=90;
      else if (LetterToDisplay  Equals  127) LetterToDisplay=57;
      else  LetterToDisplay--;
      return(LetterToDisplay);
} char LetterUp(LetterToDisplay)
char LetterToDisplay;
{
  StartMenu=EndMenu;
  if (LetterToDisplay  Equals  42) LetterToDisplay=65;
    else if (LetterToDisplay  Equals  90) LetterToDisplay=48;
    else if (LetterToDisplay  Equals  57) LetterToDisplay=127;
    else if (LetterToDisplay  Equals  127) LetterToDisplay=42;
    else LetterToDisplay++;
    return(LetterToDisplay);
} void PrintSubjectName(Pos)
char Pos;
{
  WaitTillReady();((char *)0x010000)[0xE000] = 0xC0;
  if (IDCounter NotEquals 0)
    for (loop = 0;loop < 9;loop++)
      {
      WaitTillReady();((char *)0x010000)[0xE001] = SUB[Pos].name[loop];
      }
} void ReviewPrint()
{
  ClearScreen();
  PrintMessage(StartMenu,EndMenu);
  if (StartMenu  Equals  ReviewStart)           /* print the Sub ID */
    PrintSubjectName(CurrentSub);
  else if (StartMenu  Equals  (ReviewStart+16))  /* print the min angle */
    {
       CurDeg = SUB[CurrentSub].StartDeg;Display(0);
    }
  else if (StartMenu  Equals  (ReviewStart+32))
    {
       CurDeg = SUB[CurrentSub].EndDeg;Display(0);
    }
  else                                          /* print the trial angle */
    {
      WaitTillReady();((char *)0x010000)[0xE000] = 135;
      WaitTillReady();((char *)0x010000)[0xE001] = CurrentTrial+48;
      temp = (long) (SUB[CurrentSub].trial[CurrentTrial] * 100);
      CurDeg = num = SUB[CurrentSub].trial[CurrentTrial];
      DecPart = (int) (temp - (num * 100));
      Display(1);
```

```
        }
} char GotoMenuOptions(StartMenuValue,MaxEndMenu)
int StartMenuValue,MaxEndMenu;
{
   char test,b,x,
      Done = FALSE;
   int  EndMenuValue;

StartMenu = StartMenuValue;
   EndMenuValue = StartMenuValue + 16;
   EndMenu = EndMenuValue;
   ButtonDown = TRUE;
   CurrentTrial = 0;x = 136;
   PrintMessage(StartMenu,EndMenu);
   if ( MaxEndMenu Equals IDEnd)
      {
      x = 192;
      WaitTillReady();((char *)0x010000)[0xE000] = 0x38;
      WaitTillReady();((char *)0x010000)[0xE000] = 0xC0;
      b = 42;WaitTillReady();((char *)0x010000)[0xE001] = b;
      }
   else if (MaxEndMenu Equals ReviewEnd)
      ReviewPrint();
   else if (MaxEndMenu Equals OldNum)
      {
      x = 199;
      WaitTillReady();((char *)0x010000)[0xE000] = 0x38;
      WaitTillReady();((char *)0x010000)[0xE000] = 0xC7;
      b = 78;WaitTillReady();((char *)0x010000)[0xE001] = 78;
      }
   else if (MaxEndMenu Equals RetEnd)
      PrintSubjectName(CurrentSub);
   while (Done  NotEquals  TRUE)
      {
        test = FALSE;
        while (test NotEquals TRUE)
       {
         KeyRead = P1;KeyRead = KeyRead & 7;
         if ((KeyRead Equals ENTER) And (ButtonDown Equals FALSE))
            {
              OldKey = ENTER;test = ButtonDown = TRUE;
              if (MaxEndMenu NotEquals IDEnd)
            Done = TRUE;
              else
            {
              if ( (x >= 199) And (b NotEquals 127))
                 {
                    Done=TRUE;
                    SUB[CurrentSub].name[IDCounter]=b;
```

```
        }
     else if ( (b Equals 127) And (x NotEquals 192) )
        {
           b=32;WaitTillReady();((char *)0x010000)[0xE000] = x;
           WaitTillReady();((char *)0x010000)[0xE001] = b;
           x=x-1;IDCounter--;
        }
     else if (b NotEquals 127)
        {
           SUB[CurrentSub].name[IDCounter]=b;
           IDCounter++;x++;
        }
        b = 42;
     }
  }
else if ((KeyRead Equals DOWN) And (ButtonDown Equals FALSE))
   {
     time1=0;OldKey = DOWN;
     ButtonDown = test = TRUE;
     if (MaxEndMenu Equals ReviewEnd)
    ReviewDown(StartMenuValue,MaxEndMenu);
      else if ( (MaxEndMenu Equals MenuEnd) Or
           (MaxEndMenu Equals ChPosEnd) Or
           (MaxEndMenu Equals SetUpEnd) Or
           (MaxEndMenu Equals CCEnd)
          )
    MenuDown(StartMenuValue,MaxEndMenu);
      else if (MaxEndMenu Equals OldNum)         /* Old/New */
    {
      if (b Equals 78) b++;
         else b=78;
    }
     else if (MaxEndMenu Equals RetEnd)          /* Retrieve */
    {
      if (CurrentSub Equals SubCounter) CurrentSub=0; /* was 1 */
         else CurrentSub++;
      EndMenu=StartMenu;
    }
      else b = LetterDown(b);
     StartMenu = EndMenu;EndMenu+=16;
      if ((StartMenu Equals (ReviewEnd-16)) And (CurrentTrial Equals 0))
    CurrentTrial++; /* For the first trial */
   }
else if ((KeyRead Equals UP) And (ButtonDown Equals FALSE))
   {
     time1=0;OldKey = UP;
     ButtonDown = test = TRUE;
     if (MaxEndMenu Equals ReviewEnd)
    ReviewUp(StartMenuValue,MaxEndMenu);
      else if ( (MaxEndMenu Equals MenuEnd) Or
           (MaxEndMenu Equals ChPosEnd) Or
           (MaxEndMenu Equals SetUpEnd) Or
```

```
                   (MaxEndMenu Equals CCEnd) )
            MenuUp(StartMenuValue,MaxEndMenu);
             else if (MaxEndMenu Equals OldNum)
             {
               if (b Equals 79) b--;
                 else b=79;
             }
             else if (MaxEndMenu Equals RetEnd)
             {
               if (CurrentSub Equals 0) CurrentSub=SubCounter;
                 else CurrentSub--;
               StartMenu=EndMenu;
             }
             else b = LetterUp(b);
             EndMenu = StartMenu;StartMenu-=16;
           }
         else if ( (ButtonDown Equals TRUE) And (KeyRead NotEquals OldKey) )
           ButtonDown = FALSE;
     }
     if (Done Equals FALSE)
     {
       if (MaxEndMenu Equals ReviewEnd)            /* then it's review mode */
         ReviewPrint();
       else if ( (MaxEndMenu Equals IDEnd) Or (MaxEndMenu Equals OldNum) )
         {
           WaitTillReady();((char *)0x010000)[0xE000] = x;
           WaitTillReady();((char *)0x010000)[0xE001] = b;
         }
       else if (MaxEndMenu Equals RetEnd)
         {
           ClearScreen();PrintMessage(StartMenu,EndMenu);
           PrintSubjectName(CurrentSub);
         }
       else
         {
           ClearScreen();PrintMessage(StartMenu,EndMenu);
         }
     }
    };
    if ( (MaxEndMenu Equals MenuEnd) Or
       (MaxEndMenu Equals SetUpEnd) Or
       (MaxEndMenu Equals ChPosEnd) Or
       (MaxEndMenu Equals CCEnd) )
      StartMenu = (StartMenu + 2) / 16;
    else if (MaxEndMenu Equals OldNum)
      StartMenu = b;
    return(StartMenu);
} void GotoMenu()
{
```

```
char test = FALSE,test2,Response;

while (test NotEquals TRUE)
   {
     Response=GotoMenuOptions(MenuStart,MenuEnd);
     if (Response  Equals  1) test = TRUE;
   else if (Response  Equals  2)
      {
        test2=FALSE;
        while (test2 NotEquals TRUE)
          {
         Response = GotoMenuOptions(SetUpStart,SetUpEnd);
         if (Response Equals 6)
            {
              ClearScreen();
              Response=GotoMenuOptions(NewNum,OldNum);
              if (Response Equals 78)   /* 78 = 'N ' for New */
                {
                 if ( (SubCounter Equals 0) And (NotFirstEntry Equals FALSE) )
                   {
                     GotoMenuOptions(IDStart,IDEnd);
                     NotFirstEntry=TRUE;
                   }
                 else
                    {
                      SubCounter++;IDCounter=0;CurrentSub=SubCounter;
                      SUB[CurrentSub].TrialCounter=0;set1=set2=set3=FALSE;
                      SUB[CurrentSub].StartDeg=SUB[CurrentSub].EndDeg=0;
                      GotoMenuOptions(IDStart,IDEnd);
                    }
                }
              else
                 {
                  GotoMenuOptions(RetStart,RetEnd);
                 }
              ClearScreen();
           }
         else if (Response Equals 7)
            {
              Response = GotoMenuOptions(ChPosStart,ChPosEnd);
                if (Response Equals 19) StartPos = 0;
                else if (Response Equals 20) StartPos = 90;
                else StartPos = 180;
                if (StartPos Equals 180)
              PosOffset = 0;
                else if (StartPos Equals 90) PosOffset = 270;
                else PosOffset = 180;
           }
         else if (Response Equals 8)
            {
              Response = GotoMenuOptions(CCStart,CCEnd);
              if (Response Equals 17) Rot = 1;   /* Clockwise */
```

```
                        else Rot = 0;                      /* Counterclockwise */
                    ((char *)0x010000)[0xE008] = Rot;
                }
                else if (Response Equals 9)
                    {
                        IDCounter = CurrentSub = SubCounter = 0;
                        NotFirstEntry = FALSE;
                        SUB[0].TrialCounter = 0;
                        SUB[CurrentSub].StartDeg = SUB[CurrentSub].EndDeg = 0;
                        set1=set2=set3=FALSE;
                    }
                else if (Response Equals 10)
                    test2=TRUE;
                }
            }
        else if (Response  Equals  3) DownloadData();
        else if (Response  Equals  4) GotoMenuOptions(ReviewStart,ReviewEnd);
        else if (Response  Equals  5)
            {
                if (SUB[CurrentSub].TrialCounter > 0)
                    SUB[CurrentSub].TrialCounter--;
            }
        }
    }
} float CalculateTotalTimeDiff(HighValue,LowValue)
char HighValue,LowValue;
{
    float TotalTimeDiff;
    long TimeDiff1,TimeDiff2,tempVal;

TimeDiff1 = (long) (LowValue/16);
        TimeDiff1 = (long) (TimeDiff1 * 16);
        TimeDiff1 = (long) TimeDiff1 + (LowValue%16);

TimeDiff2 = (long) (HighValue/16);
        TimeDiff2 = (long) (TimeDiff2 * 4096);
    tempVal = (long) (HighValue % 16);
        tempVal = (long) (tempVal * 256);

TimeDiff2 = (long) (TimeDiff2 + tempVal);
    TotalTimeDiff = (float) (TimeDiff1 + TimeDiff2);

return(TotalTimeDiff);
} void CalculateAng()
{
    float av,time,TotalTimeDiff,EndFrac,TimeKeep;

/*************************** FORMULA ******************************/
```

```
   TotalTimeDiff = CalculateTotalTimeDiff(TimeHigh2,TimeLow2);

EndFrac = (float) (TotalTimeDiff - TIMEINT);       /* 65320 is start count */
     EndFrac = (float) (EndFrac / (0xFFFF - TIMEINT));  /* 65535 is 0xFFF */

TimeKeep = (float) (temp - 1 + EndFrac);

time = (float) TimeKeep / 2000;
   av = (float) (( NewEnd - NewStart ) / time);

/******************************************************************/ if ( ( av > 999.0 ) || ( av < 0 ) ) av = 999.99;

CurrentTrial = SUB[0].TrialCounter;
   if (CurrentTrial < 5)
      {
         SUB[0].TrialCounter++;
         CurrentTrial++;
      }
   SUB[0].trial[CurrentTrial] = av;

temp = (long) (av * 100);
   CurDeg = num = av;
   DecPart = (int) (temp - (num * 100));
   Display(1);
   ButtonDown=TRUE;test1=FALSE;OldKey=ENTER;
   while (test1 NotEquals    TRUE)
      {
         KeyRead = P1;KeyRead = KeyRead & 7;
         if ((KeyRead  Equals   ENTER) And (ButtonDown   Equals   FALSE))
         test1=TRUE;
         else if ((KeyRead  Equals   DOWN) And (ButtonDown   Equals   FALSE))
         {
            OldKey=DOWN;time1=0;GotoMenu();test1=TRUE;
         }
         else if ((KeyRead  Equals   UP) And (ButtonDown   Equals   FALSE))
         {
            OldKey=UP;time1=0;GotoMenu();test1=TRUE;
         }
         else if ( (ButtonDown  Equals   TRUE) And (KeyRead  NotEquals    OldKey) )
         ButtonDown = FALSE;
      }
   ClearScreen();
} void GetAngVel()
{
   char test1=FALSE,test2=FALSE;
```

```
    while (test2   NotEquals   TRUE)
      {
        CurDeg = ReadPort();
        if ((test1   Equals   FALSE) And (NewStart <= CurDeg))
        {
           TH0=TIMEHIGH;TL0=TIMELOW;
           time1=0;test1=TRUE;
        }
        else if ( (NewEnd <= CurDeg) And (test1 Equals TRUE))
        {
             TimeLow2=TL0;TimeHigh2=TH0;
             temp=time1;
           CalculateAng();
           test2 = TRUE;
        }
        Display(0);
      }
} void main(void)
{
  SetBits();ClearScreen();OldKey=ENTER;
  ButtonDown=set1=set2=set3=FALSE;

/******************** CLEAN THE DATABASE ON POWER UP ***************/
  IDCounter = CurrentSub = SubCounter = 0;
  NotFirstEntry = FALSE;
  SUB[0].TrialCounter = 0;
  SUB[CurrentSub].StartDeg = SUB[CurrentSub].EndDeg = 0;
  /***************************************************************/ while (set1  NotEquals    99)    /* infinite loop */
    {
      KeyRead = P1;KeyRead = KeyRead & 7;
      CurDeg = ReadPort();
      /* power-down check point */
      if (OldDeg NotEquals CurDeg) time1=0;
      OldDeg=CurDeg;

if ( (KeyRead    Equals    ENTER) And (ButtonDown    Equals    FALSE) )
         {
         ButtonDown = TRUE;
         if (set1   Equals   FALSE)
            {
              set1 = TRUE;
              SUB[CurrentSub].StartDeg = CurDeg;
              NewStart = SUB[CurrentSub].StartDeg + 15;
              SUB[CurrentSub].EndDeg = CurDeg;
              PrintMessage(0,5);
            }
         else if (set2   Equals   FALSE)
```

```
      {
        set3=TRUE;
        PrintMessage(5,14);
        GetAngVel();
        ButtonDown=TRUE;
      };
    }
   else if ((KeyRead  Equals  DOWN)  And (ButtonDown  Equals  FALSE))
   {
     OldKey=DOWN;GotoMenu();ClearScreen();
   }
    else if ((KeyRead  Equals  UP)  And (ButtonDown  Equals  FALSE))
    {
      OldKey=UP;GotoMenu();ClearScreen();
    }
   else
     {
     if ( (ButtonDown  Equals  TRUE) And (KeyRead  NotEquals  OldKey) )
        ButtonDown = FALSE;
     if ((set1  Equals  TRUE) And (set3  Equals  FALSE))
        {
          if (CurDeg > SUB[CurrentSub].EndDeg)
            {
            SUB[CurrentSub].EndDeg = CurDeg;
            NewEnd = SUB[CurrentSub].EndDeg - 15;
            }
        }
    if (RUPT Equals 1)
       {
          ClearScreen();RUPT=0;
       }
     Display(0);
       }
    }
 }

/* PROGRAM END */
```

What is claimed is:

1. A device for measuring and displaying motion characteristics of a pair of joint-connected limb members about a joint, the device comprising:

a brace mechanism having two pivotally-connected arms forming an angle, the arms being attachable to the joint-connected limb members such that the angle between the arms is indicative of a position of one of the joint-connected limb members relative to a position of the other joint-connected limb member;

sensor means, attached to the brace mechanism, for generating a multi-bit binary signal indicative of the position of one joint-connected member relative to the position of another joint-connected member, the sensor means comprising:

a rotary encoder which generates a pair of binary pulse signals and which pivotally connects said arms of the brace mechanism;

a counter, electrically connected to the rotary encoder, which receives the pair of binary pulse signals and generates the multi-bit binary signal;

control means, electrically connected to the sensor means, for receiving the multi-bit binary signal and determining the motion characteristics therefrom;

timer means, in communication with the control means, for receiving timer start and stop signals from the control means, and for generating an elapsed time signal readable by the control means;

display means, connected to and controlled by the control means, for displaying the motion characteristics as determined by the control means;

range-determination means, connected to an controlled by the control means, for recording minimum and maximum positions attained by the joint-connected limb members during a first prespecified routine, and assigning timer start and stop positions therefrom;

velocity determination means, connected to and controlled by the control means, for determining and displaying an average angular velocity value based on an average rate of angle change between the joint-connected limb members during a second prespecified routine based on a relationship between the maximum and minimum positions and the elapsed time signal; and mode switching means, electrically connected to the control means, for enabling switching of the device between a first mode enabling the range-determination means and a second mode enabling the velocity-determination means.

2. The device of claim 1 further comprising direction switching means, electrically connected to the sensor means, for switching between a first mode enabling said sensor means to increment during clockwise rotation of said brace mechanism and a second mode enabling said sensor means to increment during counter-clockwise rotation of said brace mechanism.

3. The device of claim 1 further comprising displacement-determination means connected to and controlled by the control means, for determining an angular displacement between the joint-connected limb members.

4. The device of claim 1 further including storage means, electrically connected to said control means, for storing data related to said multi-bit binary signal and a plurality of such signals, for storing data related to said minimum and maximum positions and a plurality of such positions, and for storing data related to said average angular velocity value and a plurality of such values.

5. The device of claim 4 further including a battery unit electrically connected to the storage means enabling said device to store data when said device is powered down.

6. The device of claim 1, wherein said mode switching means comprises a plurality of control buttons, said control buttons enabling switching of said device to various modes of operation based on a particular selected control button, or on a sequence of selected control buttons, and a present mode of operation of said device.

7. The device of claim 1 further comprising a storage unit electrically connected to said control means, said storage unit storing a computer program.

8. The device of claim 1 wherein:

(a) the mode switching means further comprises a plurality of control buttons enabling switching of the device to various modes of operation based on a particular selected button or sequence of selected buttons and a present mode of operation of the device;

(b) the device further comprises:

(i) storage means, electrically connected to the control means, for storing data related to the multi-bit binary signal and a plurality of such signals, for storing data related to the minimum and maximum positions and a plurality of such positions, and for storing data related to the average angular velocity value and a plurality of such values;

(ii) a battery unit electrically connected to the storage means and enabling the device to store data when the device is powered down;

(iii) a storage unit electrically connected to the control means and storing a computer program.

9. The device of claim 8 further comprising direction switching means, electrically connected to the sensor means, for switching the sensor means between a first mode enabling said sensor means to increment during clockwise rotation of said brace mechanism and a second mode enabling said sensor means to increment during counter-clockwise rotation of said brace mechanism.

10. The device of claim 9, wherein said direction switching means comprises:

a logic circuit controlled by said control means, said logic circuit having a single output;

a flip flop controlled by said logic circuit output and generating a flip flop output;

a multiplexer controlled by said flip flop output which inverts said signals generated by said encoder.

11. The device of claim 1, wherein the timer start and stop positions are assigned so as to exclude from interest values from startup and slowdown phases of joint motion.

12. The device of claim 1, wherein:

the timer start position is at least 10 degrees beyond the minimum position;

the timer stop position is at most 10 degrees before the maximum position.

13. A method for determining an average angular velocity of a limb about a joint comprising the steps of:

providing sensor means for sensing an angular position of the limb with respect to the joint, said sensor means generating an output signal;

exercising said joint;

starting a timer when said joint reaches a first predetermined angle beyond a predetermined minimum angle of joint displacement based on the output signal of the sensor means;

stopping said timer when said joint reaches a second predetermined angle before a predetermined maximum angle of joint displacement based on the output signal of the sensor means, an interval of time between the starting and stopping of said timer comprising an elapsed time registered by said timer;

dividing a displacement, as determined by the difference between a position of the limb when the timer is started and a position of the limb when the timer is stopped, by the elapsed time registered by said timer.

14. The method of claim 13 further comprising the steps of:

assigning said first predetermined angle a value of at least 10 degrees beyond said minimum angle of joint displacement;

assigning said second predetermined angle a value of at most 10 degrees before said maximum angle of joint displacement.

15. A device for measuring and displaying motion characteristics of a pair of joint-connected limb members about a joint, the device comprising:

a brace mechanism having two pivotally-connected arms forming an angle, the arms being attachable to the joint-connected limb members such that the angle between the arms is indicative of a position of one of the joint-connected limb members relative to a position of the other joint-connected limb member;

sensor means, attached to the brace mechanism, for generating a multi-bit binary signal indicative of the position of one joint-connected member relative to the position of another joint-connected member, the sensor means comprising:

a rotary controlled mechanism generating a DC voltage signal and pivotally connecting the arms of the brace mechanism;

an analog-to-digital converter electrically connected to the rotary controlled mechanism, receiving the DC voltage signal, and generating the multi-bit binary signal indicative of the angle between the arms of the brace mechanism based on the received DC voltage signal, the angle between the arms of the brace being indicative of the position of the one joint connected member relative to the position of the other joint connected member;

control means, electrically connected to the sensor means, for receiving the multi-bit signal and determining the motion characteristics therefrom;

timer means, in communication with the control means, for receiving timer start and stop signals from the control means, and for generating an elapsed time signal readable by the control means;

display means, connected to and controlled by the control means, for displaying the motion characteristics as determined by the control means;

range-determination means, connected to and controlled by the control means, for recording minimum and maximum positions attained by the joint-connected limb members during a first prespecified routine, and assigning timer start and stop positions therefrom;

velocity determination means, connected to and controlled by the control means, for determining and displaying an average angular velocity value based on an average rate of angle change between the joint-connected limb members during a second prespecified routine based on a relationship between the maximum and minimum positions and the elapsed time signal;

mode switching means, electrically connected to the control means, for enabling switching of the device between a first mode enabling the range-determination means and a second mode enabling the velocity-determination means, the mode switching means comprising:

a plurality of control buttons enabling switching of the device to various modes of operation based on a particular selected button or sequence of selected buttons and a present mode of operation of the device;

storage means, electrically connected to the control means, for storing data related to the multi-bit binary signal and a plurality of such signals, for storing data related to the minimum and maximum positions and a plurality of such positions, and for storing data related to the average angular velocity value and a plurality of such values;

a battery unit electrically connected to the storage means and enabling the device to store data when the device is powered down;

a storage unit electrically connected to the control means and storing a computer program;

direction switching means, electrically connected to the sensor means, for switching the sensor means between a first mode enabling said sensor means to increment during clockwise rotation of said brace mechanism and a second mode enabling said sensor means to increment during counter-clockwise rotation of said brace mechanism;

a logic circuit controlled by said control means, said logic circuit having a single output;

a flip flop controlled by said logic circuit output and generating a flip flop output;

an analog switch controlled by said flip flop output which reverses a polarity of said DC voltage signal.

* * * * *